United States Patent [19]

Chu et al.

[11] Patent Number: 5,494,913
[45] Date of Patent: Feb. 27, 1996

[54] ANTIFUNGAL COMPOUNDS

[75] Inventors: Min Chu, Union; Mahesh G. Patel, Verona; Ann C. Horan, Summit; Joseph Terracciano, South Orange, all of N.J.

[73] Assignee: Schering Corporation, Kenilworth, N.J.

[21] Appl. No.: 355,147

[22] Filed: Dec. 13, 1994

[51] Int. Cl.$^6$ .................... A61K 31/435; C07D 491/16
[52] U.S. Cl. ................. 514/279; 546/37; 546/41
[58] Field of Search ................ 546/36; 514/279

[56] References Cited

U.S. PATENT DOCUMENTS 5,126,350  6/1992  Cooper .................... 514/279

OTHER PUBLICATIONS

Tetrahedron Letters, No. 18, pp. 1751–1754, (1972).
Helvetica Chimica Acta, vol. 60, Fasc. 1 (1977) No. 19 pp. 178–185.
The Journal of Antibiotics, vol. XLI, No. 6, pp. 741–750 (1988).
The Journal of Antibiotics, Apr. 1992, pp. 444–453.

*Primary Examiner*—C. Warren Ivy
*Assistant Examiner*—Evelyn Huang
*Attorney, Agent, or Firm*—Matthew Boxer

[57] ABSTRACT

Compounds of the formulas:

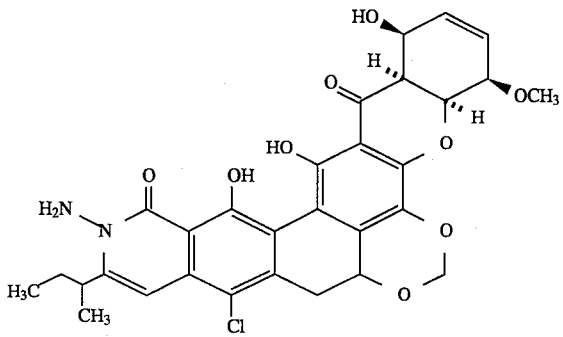

and

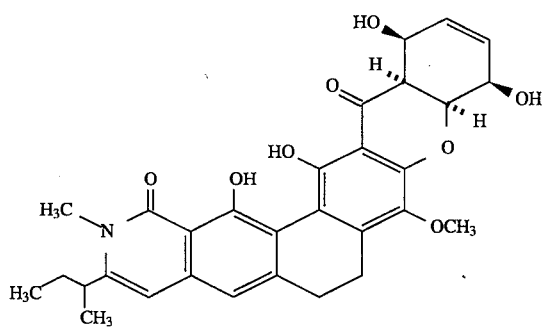

or pharmaceutically acceptable salts thereof. These compounds are obtainable by cultivation of a pure culture of Actinoplanes sp. SCC2314, ATCC 55600. These compounds are useful as antifungal agents.

6 Claims, No Drawings

ANTIFUNGAL COMPOUNDS

BRIEF SUMMARY OF THE INVENTION

Antifungal compounds A and B have been isolated from the fermentation broth of an actinomycete designated SCC2314. Compounds A and B were identified as polycyclic xanthones, related to the albofungin family of compounds. As a major component from the culture SCC2314, compound A, was found to be a potent antifungal agent against various yeasts and dermatophytes with MIC values $\leq 0.000386$ μg/mL.

This invention relates to novel antifungal compounds, A and B, to their preparation, and to pharmaceutical compositions containing such compounds. This invention also relates to a fermentation broth, and the component parts thereof obtainable by cultivation of a pure culture of Actinoplanes sp., SCC2314.

DETAILED DESCRIPTION OF THE INVENTION

As used herein, acyl means a straight or branched chain acyl, that is formyl or an alkanoyl, of 1 to 6 carbons. Exemplary of acyl are formyl, acetyl, propionyl, butyryl, and the like.

As used herein, a broken line ⁞⁞⁞⁞⁞ denotes a chemical bond below the plane of the page, while a solid line ▬▬ denotes a chemical bond above the plane of the page.

The term "pharmaceutically acceptable salt" refers to maleates, hydrochlorides, hydrobromides, sulfates, phosphates and tartrates. One skilled in the art will realize that acid additon salts of the compounds of the invention may be made with such salts whenever a basic functionality is present in a particular compound of the invention.

Certain compounds of the invention can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

As used herein,

SINEPT means Selective Insensitive Nuclei Enhanced Through Polarization Transfer;

APT means Attached Proton Test;

DEPT means Distortionless Enhancement of Polarization Transfer;

HETCOR means Heteronuclear correlation;

HMBC means heteronuclear multiple bond correlation;

HMQC means heteronuclear multiple quantum coherence;

NOE means Nuclear Overhauser Effect.

NOESY is a two-dimensional NOE; and

TMS means tetramethylsilane.

The present invention provides novel compounds A and B which have activity as anti-tumor agents and anti-fungal agents.

In another of its aspects, the present invention provides a pharmaceutical composition which comprises an effective amount of a compound of the formula A or B.

In another of its aspects, the present invention provides methods for the treatment of tumors and fungal infections.

In another of its aspects, the present invention provides a biologically pure culture of the actinomycete Actinoplanes sp., SCC2314 said culture being capable of producing the compounds A and B as defined above, in a recoverable quantity upon fermentation under aerobic conditions in an aqueous medium containing assimilable sources of nitrogen and carbon.

In another of its aspects, the present invention provides a process for the preparation of a novel broth complex which comprises cultivating the producing culture, a pure culture of Actinoplanes sp., SCC2314 in a nutrient medium under aerobic conditions until substantial activity is imparted to the medium. Specifically, we have employed a pure culture of Actinoplanes sp. SCC2314, ATCC 55600.

THE MICROORGANISM

The microorganism used for the production of the antifungal complex is a biologically pure culture of Actinoplanes sp. SCC2314, ATCC 55600. A viable culture of this microorganism was deposited on Jul. 28, 1994 in the collection of the American Type Culture Collection (ATTC) in Rockville, Md., 20852, where it has been assigned accession number ATCC 55600. Should the deposited culture become lost, destroyed or non-viable during the longer of the thirty (30) year period from the date the culture was deposited or the five (5) year period after the last request for the deposited culture on the effective life of the patent which issues from this application, the culture will be replaced upon notice by applicants or assignee(s) of this application. Subcultures of Actinoplanes sp. SCC2314, ATCC 55600 are available during the pendency of this application to one determined by the Commissioner of Patents and Trademarks to be entitled thereto under 27 CFR 1.14 and 35 USC 122 and will be available to the public without restriction once a patent based on this application is granted. Use of the microorganism is dependent on the U.S. Patent Laws.

The microorganism was isolated from a sample of soil collected in the Philippines following the procedures of Makkar & Cross (J. Appl. Bacteriol. 52, pp.209–218, 1982) and has been found to have the macroscopic, microscopic and whole cell hydrolysis properties of the genus Actinoplanes.

DESCRIPTION OF ACTINOPLANES SP. SCC2314, ATCC 55600

Source material for the following taxonomic evaluations was a frozen preparation of a pure culture of Actinoplanes sp. SCC 2314, ATCC 55600. Inoculum for the biochemical and physiological tests was prepared according to the procedures of Horan & Brodsky (Horan and Brodsky, Int. J. Syst. Bacteriol., 32, pp. 195–200, 1982). The taxonomic methods used herein are those cited by R. E. Gordon "Some criteria for the recognition of *Nocardia madurae* (Vincent) Blanchard." J. Gen. Microbiol., 45, pp. 355–364 1966; G. M. Leudemann and B. C. Brodsky "*Micromonospora carbonacea* sp. n., an everninomicin-producing organism.", Antimicrob. Agents Chemother., pp. 47–52, 1964; A. C. Horan and B. C. Brodsky "A novel antibiotic-producing Actinomadura, *Actinomadura kijaniata* sp. nov." Int. J. Syst. Bacteriol. 32, pp. 195–200, 1982; E. B. Shirling and D. Gottlieb "Methods for characterization of Streptomyces species." Int. J. Syst. Bacteriol. 16, pp. 313–340, 1966. Whole cell and cell wall analysis followed the procedures of M. P. Lechevalier "Identification of aerobic actinomycetes of clinical importance." J. Lab. Clin. Med. 71, pp. 934–944, 1968; J. L. Meyertons, D. P. Labeda, G. L. Cote and M. P. Lechevalier "A new thin layer chromatographic method for whole cell sugar analysis of Micromonospora species." The Actinomycetes, 20, pp. 182–191, 1988; and, M. P. Lechevalier and H. A. Lechevalier "Chemical composition as a criterion in the classification of aerobic actinomycetes." Int. J. Syst. Bacteriol. 20, pp. 435–443, 1970. DNA analysis by macrorestriction followed by pulsed-field gel electrophoresis was according to the procedures of M. Beyazova and M. P. Lechevalier "Taxonomic utility of restriction endonuclease fingerprinting of large DNA fragments from Streptomyces strains." Int. J. Syst. Bacteriol. 43, pp. 674–682, 1993; M. Evans and P. Dyson "Pulsed-field gel electrophoresis of *Streptomyces lividans* 66 DNA." Trends in Genetics, 9, p 72, 1993; and, B. Gravius, T. Bezmalinovic, D. Hranueli and J. Cullum "Genetic instability and strain degeneration in *Streptomyces rimosus*." Appl. Environ. Microbiol. 7, pp. 2220–2228, 1993.

The microorganism of this invention, SCC2314, ATCC 55600, is a gram-positive, filamentous microorganism that develops a moderately branching substrate mycelium with hyphae approximately 0.4 to 0.7 microns in diameter. No true aerial mycelium is present. Moderate to abundant sporangia are produced often forming a white bloom on the surface of the colony. The sporangia are irregular and borne either sessile or on short to long sporophores. When the sporangia are immersed in liquid, motile spores are released in about 60 minutes. The motile spores are round, 0.7 to 0.9 microns in diameter, to ovoid, 0.6 to 1.1 by 0.9 to 1.5 microns.

The growth characteristics of SCC2314, ATCC 55600 on various media are presented in Table 1. The names of the colors were selected after comparison with color chips from the ISCC-NBS Centroid Color Charts (Office of Standard Reference Materials NBS Circular 553, National Bureau of Standards, Washington, D.C.), the Color Harmony Manual, 4th ed. 1985 (Container Corporation of America, Chicago) and the Methuen Handbook of Colour, 3rd ed. 1981 (Eyre Methuen Ltd., London.) Macroscopically, SCC2314, ATCC 55600 grows well on most rich organic media forming orange to brown to brown-black vegetative mycelium pigments. Aerial mycelia are absent but a whitish bloom is sometimes observed. Light to medium brown soluble pigments are formed on some media. Whole cell hydrolysates contain meso-diaminopimelic acid, galactose, glucose, mannose, arabinose, ribose and xylose, a type D sugar pattern (Lechevalier & Lechevalier, 1970). The physiological and biochemical characteristics of SCC2314, ATCC 55600 are presented in Tables 2 and 3. Based on morphological and chemotaxonomic characteristics the producing culture is identified as Actinoplanes sp. SCC 2314, ATCC 55600.

Further characterization of Actinoplanes sp. SCC 2314, ATCC 55600 was accomplished using macrorestriction fingerprinting of the culture's DNA using the following restriction enzymes: Ase I, Dra I, Spe I and Ssp I. Patterns were obtained by pulsed-field gel electrophoresis in two programs which resolved two overlapping ranges of molecular weights. Molecular weights, in Kilobases, of the resulting fragments are presented in Tables 4 and 5. 92 to 600 kilobases were resolved using 25 second pulsed time at 150 milliAmps for 20 hours in TAFE buffer (10 mM Tris; 0.5 mM EDTA; 0.25 ml glacial acetic acid); 245 to 1500 kilobases were resolved using 70 second pulsed time at 150 volts for 12 hours followed by 120 second pulsed time at 150 volts for an additional 12 hours in TBE buffer (0.1 M Trizma Base; 0.1M boric acid; 0.2 mM Na$_2$EDTA).

TABLE 1

Description of Actinoplanes sp SCC2314, ATCC 55600 on various media

| Medium | | Description |
| --- | --- | --- |
| Bennett Agar | G/SM | Fair to moderate/caramel brown (Methuen 6C6) to light brown (Methuen 6D8) |
| | SPG | None |
| | SP | None |
| Glucose-Asparagine Agar | G/SM | Good/cinnamon brown (Methuen 6D6), camel (Methuen 6D4) |
| | SPG | None |
| | SP | None |
| Glycerol-Asparagine Agar (ISP 5) | G/SM | Good/teak brown (Methuen 6F5) and black mixed with camel (Methuen 6D4) |
| | SPG | Numerous |
| | SP | Faint grayish orange (Methuen 5B4) to faint brown (Methuen 6E5) |
| Glucose-Yeast Extract Agar | G/SM | Good/russet orange (CHM 4pc) and golden brown (CHM 3pi) |
| | SPG | None |
| | SP | Light brown (CHM 3ng) |
| Water Agar | G/SM | Poor/ faint grayish |
| | SPG | Moderate |
| | SP | None |
| Yeast Extract-Malt Extract Agar (ISP 2) | G/SM | Very good/brown black mixed with russet orange (CHM 4pc) and bright orange (CHM 4na) |
| | SPG | Numerous |
| | SP | Faint brownish, topaz (CHM 3ne) |
| Oatmeal Agar (ISP 3) | G/SM | Good/sepia brown (CHM 3pn) mixed with clove brown (CHM 3ni), brownish orange (Methuen 6C5), dark brown or teak (Methuen 6F5) |
| | SPG | Numerous |
| | SP | Beaver (CHM 31i) |
| Inorganic Salts-Starch Agar (ISP 4) | G/SM | Good/black (ISCC-NBS 267) and light brown (Methuen 7D5) at colony edges |
| | SPG | Numerous |
| | SP | None |
| Peptone-Yeast Extract-Iron Agar (ISP 6) | G/SM | Fair; topaz (Methuen 5C5) mixed with linoleum brown (Methuen 5E7) |
| | SPG | None |
| | SP | None |
| Gause Mineral Agar I | G/SM | Good/brownish black (ISCC-NBS 65) and dark grayish brown (ISCC-NBS 62) |
| | SPG | None |
| | SP | None |
| Czapek Peptone Agar | G/SM | Fair/reddish orange (Methuen 7B7) mixed with brownish orange (Methuen 7C6) |
| | SPG | None |
| | SP | None |
| Sporulation Agar (ATCC Medium 5) | G/SM | Very good/brownish black (ISCC-NBS 65) with brownish orange edges (ISCC-NBS 54) |
| | SPG | Numerous |
| | SP | Moderate brown (ISCC-NBS 58) |
| ATCC Medium 172 | G/SM | Excellent/brownish black (ISCC-NBS 65) and deep brown (ISCC-NBS 56), reddish orange (Methuen 7B8) turning brownish orange and dark brown (Methuen 7F4) |
| | SPG | Impossible to observe |
| | SP | Golden brown (CHM 3pg), topaz (CHM 3ne) |
| Nutrient Agar | G/SM | Fair/reddish golden (Methuen 6C7), cinnamon brown (Methuen 6D6) mixed with brownish black (ISCC-NBS 65) |
| | SPG | None |
| | SP | None |

TABLE 1-continued

Description of Actinoplanes sp SCC2314,
ATCC 55600 on various media

| Medium | Description |
|---|---|

G/SM - Amount of Substrate Growth/Color of Substrate Mycelium; SPG - Sporangia; SP - Soluble Pigment

TABLE 2

Acid Production and Carbohydrate Utilization
by Actinoplanes sp, SCC 2314, ATCC 55600

| Carbohydrate | Acid Production | Carbohydrate Utilization |
|---|---|---|
| Adonitol | − | − |
| D-Amygdalin | − | + |
| D-Arabinose | + | +/− |
| L-Arabinose | + | + |
| Dextrin | + | + |
| Dulcitol | +/− | +/− |
| i-Erythrol | − | − |
| D-Fructose | + | + |
| L-Fucose | + | − |
| D-Galactose | + | + |
| Glucose | + | + |
| Glycerol | + | + |
| i-Inositol | − | − |
| Inulin | + | + |
| Lactose | + | + |
| Maltose | + | + |
| D-Mannitol | + | + |
| D-Mannose | + | + |
| D-Melezitose | + | + |
| D-Melibiose | + | + |
| α-methyl-D-Glucoside | + | + |
| α-methyl-D-Mannoside | + | + |
| D-Raffinose | + | + |
| L-Rhamnose | + | + |
| D-Ribose | +/− | +/− |
| Salicin | + | + |
| D-Sorbitol | + | + |
| L-Sorbose | − | − |
| Sucrose | + | + |
| Trehalose | + | + |
| D-Xylose | + | + |

+ positive; − negative; +/− doubtful

TABLE 3

Physiological Characteristics
of Actinoplanes sp. SCC2314 ATCC 55600

| Test | Result |
|---|---|
| Formation of Melanin | |
| Peptone-yeast extract iron agar (ISP 6) | − |
| Tyrosine agar (ISP 7) | + |
| Liquefaction of Gelatin | + |
| Hydrolysis or Decomposition of: | |
| Adenine | − |
| Allantoin | − |
| Casein | + |
| Hippurate | + |
| Hydantoin | − |
| Hypoxanthine | − |
| L-Tyrosine | + |
| Potato starch | + |
| Urea | + |
| Xanthine | − |
| Xylan | + |
| Reduction of nitrate | + |
| Growth on NaCl: | |

TABLE 3-continued

Physiological Characteristics
of Actinoplanes sp. SCC2314 ATCC 55600

| Test | Result |
|---|---|
| 3% | + |
| 4% | +/− |
| 5% | − |
| Growth at: | |
| 10° C. | − |
| 15° C. | + |
| 28° C. | + |
| 37° C. | + |
| 40° C. | + |
| 45° C. | + |
| 50° C. | − |
| Utilization of: | |
| Acetate | + |
| Benzoate | − |
| Butyrate | − |
| Caprylate | + |
| Citrate | + |
| Formate | + |
| Glutamate | + |
| Gluconate | + |
| Glucuronate | + |
| Lactate | + |
| Malate | + |
| Malonate | +/− |
| Oleate | − |
| Oxalate | +/− |
| Propionate | + |
| Pyruvate | + |
| Succinate | + |
| Tartrate | − |
| Fumarate | + |
| α-keto-Glutarate | + |
| Calcium glycerate | + |

+ positive; − negative; +/− doubtful

TABLE 4

Fragments from Actinoplanes sp.
SCC2314 DNA after restriction with Dra 1.

| STANDARD Saccharomyces cerevisiae DNA (Mol Wt in Kilobases) | SAMPLE Actinoplanes sp. SCC2314 DNA restricted with Dra 1 (Mol Wt in Kilobases) |
|---|---|
| 1125 | |
| 1020 | |
| 945 | |
| | 903 |
| | 850 |
| 800 | |
| 770 | |
| | 705 |
| 700 | |
| 630 | |
| 580 | |
| | 544 |
| 460 | |
| | 432 |
| 370 | |
| | 363 |
| 290 | |
| | 275 |
| 245 | |
| | 235 |

Conditions: 70 sec pulsed time at 150 v/12 hrs followed by 120 sec pulsed time at 150 v/20 hours in TBE buffer.
9 bands in the window of 200 to 1500 Kilobases. Bands occur outside of the window but were not well resolved under the conditions described.

TABLE 5

Fragments from Actinoplanes sp. SCC2314 DNA after restriction with Ase I, Spe I and Ssp I.

| STANDARD | SAMPLES: Actinoplanes sp. SCC2314 | | |
|---|---|---|---|
| LAMBDA CONCATAMER Mol. Wt. Kilobases | Asn I Mol. Wt. Kilobases | Spe I Mol. Wt. Kilobases | Ssp I Mol. Wt. Kilobases |
|  | 606 | 619 | 607 |
| 598 |  |  |  |
| 552 |  |  |  |
|  |  |  | 546 |
|  | 525 | 527 |  |
|  | 512 |  |  |
| 506 |  |  |  |
|  |  | 501 |  |
|  |  | 492 | 495 |
|  |  | 482 | 482 |
|  | 478 | 479 |  |
|  |  | 465 |  |
| 460 |  |  |  |
|  |  |  | 451 |
|  | 428 |  |  |
| 414 |  |  |  |
|  |  |  | 406 |
|  |  | 384 |  |
|  |  |  | 362 |
| 368 |  |  |  |
|  |  | 356 |  |
|  |  | 330 |  |
| 322 |  |  | 324 |
|  | 306 |  |  |
|  | 289 | 281 |  |
| 276 | 273 |  |  |
|  |  |  | 266 |
|  |  |  | 251 |
| 230 |  |  |  |
|  | 213 |  | 211 |
|  |  | 199 |  |
|  | 189 |  | 192 |
| 184 |  | 184 |  |
|  | 150 |  | 148 |
| 138 |  | 135 |  |
|  | 130 |  |  |
| 92 | 90 |  |  |

Conditions: 25 sec pulsed time at 150 mA/20 hrs in Tris-acetate buffer. The program resolves molecular weights of 92 to 600 kilobases. Bands occur outside of the window but were not well resolved under the conditions described.

FERMENTATION

The organism Actinoplanes sp. SCC2314, ATCC 55600 when fermented under controlled conditions in an aqueous medium, containing assimilable sources of carbon, nitrogen and inorganic substances produce sufficient quantities of antifungal compound A and B.

The fermentation which produces the antifungal compounds is initated by the production of an inoculum which is usually produced in two stages. A suitable medium for preparing such inoculum is set forth below as Medium A. The proper pH ranges are usually maintained by incorporation of suitable buffers, such as calcium carbonate into the medium.

The media were sterilized and cooled prior to inoculation and fermentation stock cultures were stored as frozen whole broths at subzero temperatures prior to use.

Inoculation preparation (First Stage)

Inoculum preparation was carried out in two stages for large scale fermentation (8 L). Suitable nutrients for preparing the inocula are listed below:

| Inoculum Medium A | |
|---|---|
| Beef Extract | 3 g/L |
| Tryptone | 5 g/L |
| Yeast Extract | 5 g/L |
| Cerelose | 1 g/L |
| Soluble Starch | 24 g/L |
| $CaCO_3$ | 2 g/L |
| Tap water | 1 L |
| Antifoam | 1 ml/L |
| Pre-sterilization | pH 7.0 |

Two and a half milliters of freshly thawed whole broth were used to inculate 70 mls of the above listed inoculum Medium A. The 250 ml Erlenmeyer flasks were incubated at 30° C. for 96 hours on a shaker at 250 rpm having a 2 inch throw.

Second Inoculum preparation

A 250 ml Erlenmeyer flask containing 70 mls of sterile inoculum Medium A was inoculated using 5% of the first stage inoculum. The procedure for the first inoculum stage was followed.

ANTIFUNGAL PRODUCTION (FERMENTATION) STAGE

The following fermentation medum B has been found to produce the compounds of this invention:

| Fermentation medum B | |
|---|---|
| Soluble Starch | 15 g/L |
| Sucrose | 5 g/L |
| Dextrose | 5 g/L |
| Soy Peptone | 7.5 g/L |
| Corn Steep Liquor | 5 ml/L |
| $K_2HPO_4$ | 1.5 g/L |
| NaCl | 0.5 g/L |
| Mineral Solution | 10 ml/L |
| Tap Water | 1 L |
| Pre-sterilization | pH 7.0 |
| Mineral solution g/l | |
| $ZnSO_4.7H_2O$ | 2.8 g |
| Ferric Ammonium Citrate | 2.7 g |
| $CuSO_4.5H_2O$ | 0.125 g |
| $MnSO_4.H_2O$ | 1.0 g |
| $Co_2Cl_2.6H_2O$ | 0.1 g |
| $Na_2B_4O_7.H_2O$ | 0.088 g |
| $Na_2MoO_4.2H_2O$ | 0.05 g |

A 2 L Erienmeyer flask containing 500 mls of sterile fermentation medium B was inoculated using 5% of the second stage inoculum. The 2 L Erlenmeyer flask was incubated at 30° C. for 96 hours on a shaker at 250 rpm having a 2 inch throw. After 24 hours, 50 gms wet weight of washed sterile XAD-16 resin was added to the 2 L Erlenmeyer flask and the fermentation was continued for the remaining 72 hours. The antifungal activity was monitored during the course of fermentation by disking on *Candida albicans* agar diffusion plates.

ISOLATION AND PURIFICATION OF PRODUCTS

The isolation procedure of compounds A and B is summarized in Scheme 1. The XAD-16 resin (800 ml), which was introduced during the fermentation process to stabilize and absorb the antifungal active components, was separated from the culture broth (8 L) by paper filtration. After removal of inactive filtrate, XAD-16 resin was thoroughly washed with water. The active resin was extracted with EtOAc (2×2 L). The EtOAc solution was dried over anhydrous $Na_2SO_4$, filtered and concentrated in vacuo. The residue (1.9 g), which was redissolved in $CH_2Cl_2$-MeOH (7:3), was loaded on a Sephadex LH-20 column and eluted with $CH_2Cl_2$-MeOH (7:3). The combined antifungal active fractions (1 g) were further chromatographed on a Sephadex LH-20 column eluting with $CH_2Cl_2$-MeOH (1:1). Pure compound A (30 mg) was obtained as a yellow-brown solid from the active complex (392 mg) by chromatography on a Sephadex LH-20 column eluting with $CH_2Cl_2$-MeOH (3:7).

The mixture, which contained compound B, was further purified by a polyvinyl alcohol coated silica gel column with a methanol: 1-chlorobutane solvent system (YMC, semi-preparative PVA-SIL column 20×250 mm, S-5, 3–4% MeOH in n-BuCl with a linear gradient in 20 minutes, 8 mL/min flow rate, UV detection at 225 nm, $t_R$=22.24 minutes). Pure compound B (5 mg) was obtained as a yellow amorphous powder.

In this process some restrictions should be noted. The antifungal components were unstable in aqueous media, therefore, only organic solvent was utilized in the isolation procedure. In addition, a silica gel column was not suitable for the separation because of observed decomposition under acidic conditions.

Scheme 1-Isolation of Compound A and B from Culture SCC 2314

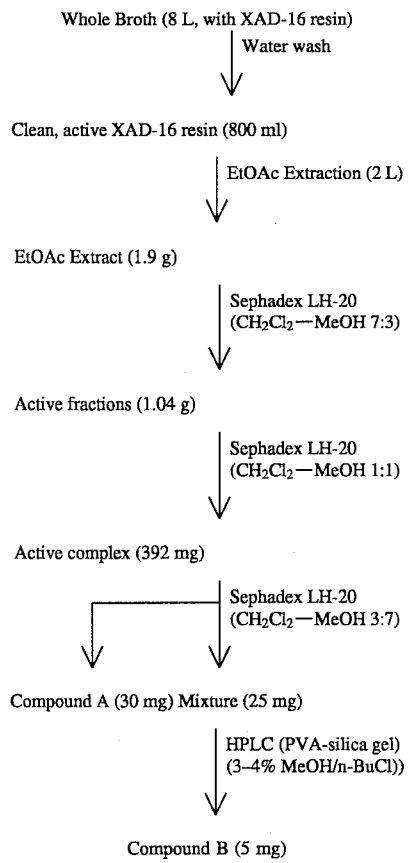

THE STRUCTURAL ELUCIDATION OF THE COMPOUNDS OF THE INVENTION

Structural Elucidation Of Compound A

The compound A, mp=201°–203° C. (dec.), $[\alpha]^{23}_D$-558° ($CHCl_3$), is soluble in $CHCl_3$, DMSO, $CH_2Cl_2$ and MeOH, insoluble in hexane and water. It stained brown in the presence of iodine vapor and tested Rydon positive. The $R_f$ value of compound A is 0.85 on silica gel TLC plate (Whatman, LK6DF, developing solvent: $CHCl_3$-MeOH-hexane-$H_2O$, 3:3:1:1).

The molecular weight of compound A was determined to be 596 on the basis of mass spectrum that showed a protonated molecular ion m/z 597 $(M+H)^+$ in FAB-MS. The chlorine containing ion clusters were also observed (the ratio of intensity for m/z 597 and m/z 599, 3:1 ). The molecular formula was deduced as $C_{30}H_{29}N_2O_9Cl$ by means of high resolution mass spectrum (HRFAB-MS: m/z 597.1609 $(M+H)^+$, $\Delta 5.1$ mmu), as well as $^1H$ and $^{13}C$ NMR data. Elemental analysis of compound A provided confirmatory evidence for the above formula (Calcd. for $C_{30}H_{29}N_2O_9Cl$: C 60.04 H 4.87, N 4.70, Cl 5.87. Found: C 60.05, H 4.79, N 4.44, Cl 5.46). The IR spectrum indicated the presence of hydroxyl (3450 $cm^{-1}$), conjugated carbonyl (1640 $cm^{-1}$) and γ-pyrone (1570 $cm^{-1}$) functionalities. The UV spectrum was similar to polycyclic xanthone antibiotics showing maximum absorptions at 215, 251, 270 (Sh.), 326 and 393 nm.

The $^1H$ and $^{13}C$ NMR spectra of compound A along with the assignments of hydrogens and carbons are given in Tables 6 and 7 respectively. All assignments of protons and carbons are confirmed based on HMBC data which are given in Table 8.

The detailed study of NOESY and difference NOE spectral data led to the establishment of the relative stereochemistry of the G ring. As shown in Table 9, a nuclear Overhauser effect (NOE) was observed for 24-H and 28-H when the 23-H signal was irradiated. The NOE was also detected for 23-H and 27-H when the 28-H signal was irradiated in difference NOE experiment. Thus, these four methine protons were assigned to all cis on G ring. This assignment was further confirmed by the observation of NOE cross peaks between 24-H and 23-H, 23-H and 28-H, as well as 28-H and 27-H in NOESY experiment.

TABLE 6

| $^1H$ NMR spectral data of compound A[a] | | | |
|---|---|---|---|
| Proton | δ(J = Hz) | Proton | δ(J = Hz) |
| 2-$NH_2$ | 4.87 br. s[b] | 24-$OCH_3$ | 3.62 s |
| 4-H | 6.80 s | 25-H | 6.00 dddd(1.8, 1.8, 3.7, 10.1) |
| 8-$H_{ax}$ | 2.68 dd(12.9, 14.7) | 26-H | 5.95 dd(1.8, 10.1) |
| 8-$H_{eq}$ | 3.82 dd(4.8, 14.7) | 27-H | 4.60 br.d(8.5) |
| 9-H | 4.78 dd(4.8, 12.9) | 27-OH | 3.78 br.s[b] |
| 11-$H_{ax}$ | 5.22 d(5.9) | 28-H | 3.45 dd(8.5, 14.2) |
| 11-$H_{eq}$ | 5.50 d(5.9) | 30-H | 3.45 m |
| 17-OH | 13.44 br.s[b] | 31-$CH_2$ | 1.60, 1.80 AB, m |
| 19-OH | 11.84 s[b] | 32-$CH_3$ | 0.98 t(7.4) |
| 23-H | 4.49 dd(3.7, 14.2) | 33-$CH_3$ | 1.33 d(6.8) |
| 24-H | 4.15 dd(3.7, 8.4) | | |

[a]Recorded at 400 MHz in $CDCl_3$, Chemical shift (δ) in ppm from TMS
[b]Exchangeable with $CD_3OD$

TABLE 7

13C NMR spectral data of compound A[a]

| Position | δ | Position | δ |
|---|---|---|---|
| C-1 | 164.3s[b] | C-19 | 151.7s |
| C-3 | 150.4 s | C-20 | 106.7s |
| C-4 | 100.0 d | C-21 | 137.9s |
| C-5 | 133.5 s | C-23 | 77.7d |
| C-6 | 116.6 s | C-24 | 71.7d |
| C-7 | 148.0 s | C-25 | 133.0d |
| C-8 | 33.2 t | C-26 | 124.1d |
| C-9 | 72.2 d | C-27 | 67.5d |
| C-11 | 90.5 t | C-28 | 46.5d |
| C-13 | 132.9 s | C-29 | 200.4s |
| C-14 | 130.9 s | C-30 | 35.4d |
| C-15 | 109.4 s | C-31 | 28.5t |
| C-16 | 114.6 s | C-32 | 11.2q |
| C-17 | 155.5 s | C-33 | 18.7q |
| C-18 | 109.7 s | 24-OCH₃ | 58.0q |

[a]Recorded at 100 MHz in CDCl₃, Chemical shift (δ) in ppm from TMS
[b]Multiplicity was determined by DEPT data.

TABLE 8

HMBC Data for compound A

| Proton | 2-bond correlation | 3-bond correlation | 4-bond correlation |
|---|---|---|---|
| 2-NH₂ | | C-1, C-3 | |
| 4-H | C-3 | C-6, C-18, C-30 | C-1, C-17 |
| 8-H$_{ax}$* | C-9 | C-6, C-16 | C-5, C-17 |
| 8-H$_{eq}$* | C-9 | C-6, C-16 | C-5 |
| 9-H | C-8 | C-13, C-15 | C-19, C-21 |
| 11-H$_{ax}$ | | C-9, C-13 | |
| 11-H$_{eq}$ | | C-9, C-13 | |
| 17-OH | C-17 | C-16, C-18 | |
| 19-OH*** | C-19 | C-15, C-20 | C-29 |
| 23-H | C-24, C-28 | C-27, C-29 | |
| 24-H | C-23, C-25 | C-26, C-28, 24-OCH₃ | C-29 |
| 24-OCH₃ | | C-24 | |
| 25-H | C-24 | C-23, C-27 | |
| 26-H | C-27 | C-24, C-28 | |
| 27-H | C-26, C-28 | C-25, C-29 | C-23 |
| 28-H | C-23, C-27, C-29 | C-24 | |
| 30-H | C-3, C-32, C-33 | C-4, C-32 | C-5 |
| 31-CH₂ | C-30, C-32 | C-3, C-33 | |
| 32-CH₃ | C-31 | C-30 | |
| 33-CH₃ | C-30 | C-3, C-31 | |

*The 5-bond correlations of 8-H$_{ax}$ and 8-H$_{eq}$ to C-21 were observed. As used herein, "eq" means equatorial and "ax" means axial.
**The 5-bond correlations of 9-H to C-5 and C-20 were observed.
***A 4-bond correlation of 19-OH to C-29 was observed as a weak cross peak.

TABLE 9

NOESY and difference NOE correlation data for compound A

| Position | NOESY | Difference NOE |
|---|---|---|
| 2-NH₂ | 30-H | |
| 4-H | 30-H, 31-H, 33-H | 30-H, 31-H, 32-H |
| 8-H$_{ax}$ | 8-H$_{eq}$ | |
| 8-H$_{eq}$ | 8-H$_{ax}$, 9-H | |
| 9-H | 8-H$_{eq}$, 11-H$_{ax}$ | 8-H$_{eq}$, 11-H$_{ax}$ |
| 11-H$_{ax}$ | 9-H, 11-H$_{ea}$ | |
| 11-H$_{eq}$ | 11-H$_{ax}$ | |
| 23-H | 24-H, 27-H, 28-H | 24-H, 28-H |
| 24-H | 23-H, 25-H, 24-OCH₂ | 23-H, 25-H, 24-OCH₃ |
| 25-H | 24-H, 26-H | |
| 26-H | 25-H, 27-H | |
| 27-H | 23-H, 26-H, 27-OH | |
| 28-H | 23-H | 23-H, 27-H |
| 30-H | 2-NH₂, 33-H | 4-H, 31-H, 33-H |

TABLE 9-continued

NOESY and difference NOE correlation data for compound A

| Position | NOESY | Difference NOE |
|---|---|---|
| 31-H | 32-H | |
| 32-H | 30-H, 31-H | |
| 33-H | 30-H | |

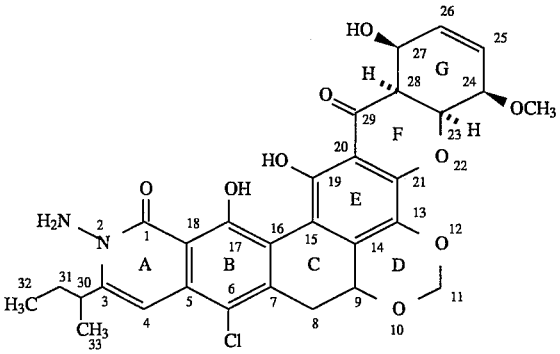

Structural Elucidation of Compound B

The compound B has a mp=195° C., [α]²³$_D$+212.50° (c 0.2, CHCl₃), is soluble in CHCl₃, CH₂Cl₂, DMSO, and MeOH, insoluble in hexane and water. The R$_f$ value of compound B is 0.75 on a silica gel, TLC plate.

The UV spectrum of compound B showed maxima at 260, 290 (sh), 315, 354 (sh) and 365 nm. In the IR spectrum, strong absorption bands at 3446 (—OH groups), 1646 and 1593 cm⁻¹ (two conjugated C=O functionalities) were observed and together with the UV spectrum suggested the presence of a polycyclic xanthone moiety, which is similar to the major component, compound A.

Molecular weight determination of compound B by FAB-MS gave rise to a protonated molecular ion at m/z 534 (M+H)⁺, and a sodium adduct ion at m/z 556 (M+Na)⁺ by introducing NaCl salt in the matrix. The molecular weight of 533 was confirmed by a negative-mode FAB-MS technique showing a strong deprotonated ion at m/z 532 (M-H)⁺. In addition, a negative data of elemental analysis for halogen atoms, together with the absence of halogen cluster ions in mass spectra, indicated compound B as a non-halogenated compound. The exact mass of the protonated molecular ion of compound B was found as m/z 534.2102 with the most likely molecular formula being C₃₀H₃₁NO₈ (calcd. for C₃₀H₃₁ NO₈: m/z 534.2128).

The ¹H and ¹³C NMR spectra of compound B along with the assignments of hydrogens and carbons are given in Tables 10 and 11 respectively.

The assignments of each individual proton and carbon in compound B were supported by a combination of DEPT, COSY, HETCOR, HMQC and HMBC experiments.

TABLE 10

¹HNMR Spectral Data of Compound B[a]

| Proton | δ(CDCl₃) | δ(C₆D₆) |
|---|---|---|
| 2-NCH₃ | 3.72 s | 2.97 s |
| 4-H | 6.47 s | 6.08 s |
| 6-H | 6.92 s | 6.55 s |
| 8-H$_{ax}$ | 2.83 m | 2.51 m |
| 8-H$_{eq}$ | 2.83 m | 2.51 m |

TABLE 10-continued

¹HNMR Spectral Data of Compound B[a]

| Proton | δ(CDCl₃) | δ(C₆D₆) |
|---|---|---|
| 9-CH₂ | —[b] | —[b,c] |
| 11-CH₂ | — | — |
| 13-OCH₃ | 3.88 s | 3.50 s |
| 17-OH | 14.05 s | 14.75 s |
| 19-OH | 12.12 br.s | 12.58 br.s |
| 23-H | 4.48 dd(3.6, 14.0) | 3.38 br.d (14.0) |
| 24-H | 4.69 t(4.4) | 3.96 t(4.2) |
| 24-OH | 2.61 br.s | 2.17 br.s |
| 25-H | 6.08 m | 5.49 m |
| 26-H | 6.08 m | 5.75 dd (2.0, 10.0) |
| 27-H | 4.70 br.d (8.8) | 4.16 br.d(8.6) |
| 27-OH | 4.05 br.s | 3.78 br.s |
| 28-H | 3.43 dd(8.8, 14.0) | 3.03 dd(8.6, 14.0) |
| 30-H | 2.94 m | 2.08 m |
| 31-CH₂ | 1.70,1.86 AB, m | 1.09,1.29, AB, m |
| 32-CH₃ | 1.09 t(7.4) | 0.64 t(7.5) |
| 33-CH₃ | 1.40 d(6.8) | 0.82 d(6.9) |

[a]Recorded at 400 MHz at 25° C. chemical shifts (δ) in ppm from TMS.
[b]The methylene protons at 9-position were not observed at 25° C.
[c]The methylene protons at 9-position were observed at 82.23, 3.23 at −25° C. The assignment of these two protons was confirmed by NOESY and HMQC experiments at −25° C.

TABLE 11

¹³C NMR Spectral Data of Compound B[a,b]

| Position | CDCl₃ | C₆D₆ |
|---|---|---|
| C-1 | 167.1 s | 167.3 s |
| C-3 | 148.2 s | 147.8 s |
| C-4 | 104.2 d | 103.8 d |
| C-5 | 136.9 s | 136.9 s |
| C-6 | 113.0 d | 112.7 d |
| C-7 | 146.5 s | 146.6 s |
| C-8 | 30.6 t | 30.7 t |
| C-9 | 23.9s[c] | 24.2s[c] |
| C-11 | — | — |
| C-13 | 136.5 s | 136.9 s |
| C-14 | 146.4 s | 145.9 s |
| C-15 | 114.7 s | 115.1 s |
| C-16 | 114.9 s | 115.9 s |
| C-17 | 157.8 s | 159.3 s |
| C-18 | 109.9 s | 110.6 s |
| C-19 | 155.2 s | 156.4 s |
| C-20 | 106.9 s | 107.4 s |
| C-21 | 152.2 s | 152.4 s |
| C-23 | 77.3 d | 77.2 d |
| C-24 | 64.1 d | 64.2 d |
| C-25 | 134.2 d | 134.0 d |
| C-26 | 125.4 d | 127.5 d |
| C-27 | 68.0 d | 68.1 d |
| C-28 | 46.4 d | 46.5 d |
| C-29 | 200.4 s | 201.0 s |
| C-30 | 36.7 d | 36.4 d |
| C-31 | 29.4 t | 29.2 t |
| C-32 | 11.8 q | 11.6 q |
| C-33 | 20.0 q | 19.6 q |
| 2-NCH₃ | 29.9 q | 29.3 q |
| 13-OCH₃ | 61.6 q | 61.0 q |
| 24-OCH₃ | — | — |

[a]Recorded at 100 MHz at 25° C. chemical shifts (δ) in ppm from TMS.
[b]Multiplicity was determined by DEPT experiment.
[c]The C-9 signal was observed as a methylene carbon based on DEPT experiment at −25° C. The methylene carbon assignment for C-9 was also confirmed by the observation of a triplet(J = 130 Hz) in non-decoupled carbon spectrum, SFORD experiment, at 25° C.

TABLE 12

HMBC Data for Compound B[a,b]

| Proton | 2-bond correlation | 3-bond correlation | 4-bond correlation |
|---|---|---|---|
| 2-NCH₃ | | C-1, C-3 | |
| 4-H | C-3, C-5 | C-6, C-30 | C-17 |
| 6-H | C-5, C-7 | C-4, C-8, C-16 | C-1, C-17 |
| 8-CH₂ | C-7, C-9 | C-14, C-16 | C-15 |
| 13-OCH₃ | | C-13 | |
| 17-OH | C-17 | C-16, C-18 | |
| 24-H | C-23, C-25 | C-26, C-28 | |
| 25-H | C-24 | C-23, C-27 | |
| 26-H | | C-24, C-28 | |
| 27-H | C-26 | C-25, C-29 | |
| 28-H | C-23, C-27, C-29 | C-24 | |
| 30-H | C-3, C-31, C-33 | C-4, C-32 | |
| 31-H | C-30, C-32 | C-3, C-33 | |
| 32-H | C-31 | C-30 | |
| 33-H | C-30 | C-3, C-31 | |

[a]The spectrum recorded on GE Omega (400 MHz) in C₆D₆ at 25° C.
[b]The correlations between H-23 and its adjacent carbons were not observed.

Based upon the above spectral data, the structure just below was assigned to compound B.

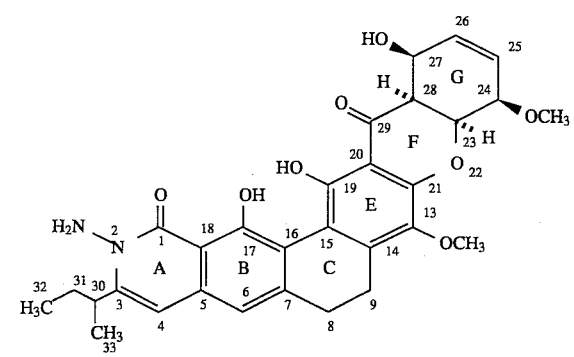

Compounds A and B of the invention were tested in standard antifungal assays and data from these tests appear in the Table 13 just below.

TABLE 13

In vitro activity of compounds
A and B and Albofungin against various fungi

| | Geometric means MICs μg/ml, 48/72 hr) | | |
|---|---|---|---|
| | (No. Of Strains) | Albofungin | A | B |
| SDB (5.7) | | | | |
| C. albicans & C. tropicalis | 8 | <0.00055 | <0.000386 | 0.017 |
| Other Candida | 6 | <0.00099 | <0.00128 | 0.0312 |
| Dermatophytes | 5 | 0.0359 | 0.00764 | 0.1436 |
| Aspergillus | 3 | 0.125 | 0.0248 | 0.7937 |
| EMEM (7.0) | 9 | <0.0182 | <2.16 | <0.1350 |
| C. albicans & C. tropicalis | | | | |

SDB means Sabourand dextrose broth, pH 5.7;
EMEM means Eagle's minimum essential medium, pH 7.0.

Compounds A and B demonstrated in vivo $LD_{50}$ values which range from about 1 to about 25 mpk iv. "mpk" means mg. per kg.

One skilled in the art would be able to employ compositions containing compounds of the invention to treat fungus, and infection.

Compounds of the invention can be administered as tablets, capsules, suspensions or aerosols. They can be administered orally, subcutaneously, intravenously, or by inhalation.

While effective amounts may vary, as conditions in which such compositions are used vary, a minimal dosage required for antifungal activity is generally between 1 and 1000 milligrams one to four times daily.

The compounds of this invention can be administered in any number of conventional dosage forms, e.g., topical, oral, parenteral, rectal, transdermal, and the like. Oral or rectal dosage forms include capsules, tablets, pills, powders, cachets, and suppositories. Liquid oral dosage forms include solutions and suspensions. Parenteral preparations include sterile solutions and suspensions. Topical dosage forms can be aerosols, creams, ointments, lotions, transdermal devices (e.g., of the conventional patch or matrix type) and the like.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, coloring agents, stabilizing agents, emulsifying agents, dispersing agents, suspending agents, perfumes, preservatives lubricants, etc.

Suitable pharmaceutical acceptable solid carriers are magnesium carbonate, magnesium stearate, talc, sugar, lactose, pectin, dextrin, starch, gelatin, tragacanth, methylcellulose, sodium carboxymethylcellulose, low melting waxes, cocoa butter and the like. Capsules can be made wherein the active compound is inserted into the capsules along with a pharmaceutically acceptable carrier. The active compounds of this invention can be mixed with pharmaceutically acceptable excipients or be used in finely divided powder form without excipients for inclusion into the capsules. Similarly, cachets are included.

Liquid form preparations include solutions, suspensions and emulsions such as water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in finely divided form in water with viscous material, i.e., pharmaceutically acceptable natural or synthetic gums, resins, methylcellulose, sodium carboxymethylcellulose and other well-known suspending agents.

Formulations for topical application may include the above liquid forms, as well as creams, aerosols, sprays, dusts, powders, lotions and ointments which are prepared by combining an active ingredient according to this invention with conventional pharmaceutical acceptable diluents and carriers commonly used in topical, dry, liquid, cream and aerosol formulations. Ointment and creams may, for example, be formulated with an aqueous or oily base with the addition of suitable thickening and/or gelling agents.

Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oil base and will, in general, also include one or more of pharmaceutically acceptable stabilizing agents, emulsifying agents, dispersing agents, suspending agents, thickening agents, coloring agents, perfumes and the like.

Powders may be formed with the aid of any suitable pharmaceutically acceptable powder base, e.g., talc, lactose, starch, etc. Drops may be formulated with an aqueous base or non-aqueous base also comprising one or more pharmaceutically acceptable dispersing agents, suspending agents, solubilizing agents, etc.

The topical pharmaceutical compositions may also include one or more preservatives or bacteriostatic agents, e.g., methyl hydroxybenzoate, propyl hydroxybenzoate, chlorocresol, benzalkonium chlorides, etc.

The topical pharmaceutical compositions may also contain an active compound of this invention in combination with other active ingredients such as antimicrobial agents, particularly antibiotics, anesthetics, analgesics and antipruritic agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses under conditions which retard possible decomposition. The solid form preparations intended to be converted to liquid form may contain, in addition to the active material, pharmaceutically acceptable flavorants, colorants, stabilizers, buffers, artificial and natural sweeteners, dispersants, thickeners, sol ubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of this invention may also be deliverable transdermally for systemic distribution. The transdermal compositions can take the form of creams, lotions and/or emulsions and can be included in a transdermal patch of the matrix or reservoir type as are conventional in the art for this purpose.

A composition of the invention comprises a therapeutically effective amount of a compound of the invention in combination with a pharmaceutically acceptable carrier material.

The compounds of this invention may be administered by any conventional mode of administration by employing a therapeutically effective amount of a compound of this invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

What is claimed is:

1. The compound of the formula

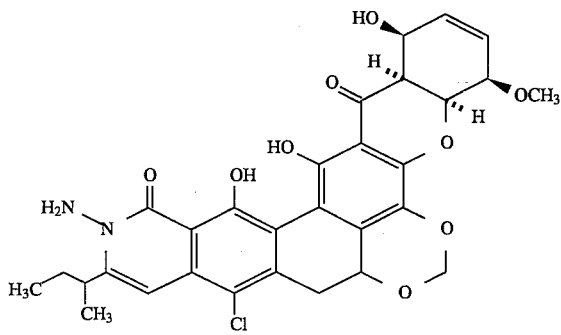

or a pharmaceutically acceptable salt thereof.

2. The compound of the formula

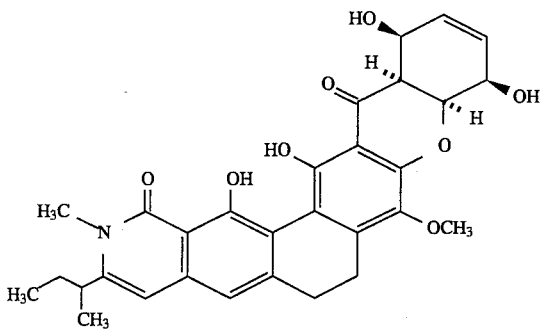

or a pharmaceutically acceptable salt thereof.

3. A pharmaceutical composition comprising an antifungal effective amount of a compound of claim 1 and a pharmaceutically acceptable carrier material.

4. A pharmaceutical composition comprising an antifungal effective amount of a compound of claim 2 and a pharmaceutically acceptable carrier material.

5. A method for treating fungal infections which comprises administering an antifungal, effective amount of a compound of claim 1.

6. A method for treating fungal infections which comprises administering an antifungal, effective amount of a compound of claim 2.

* * * * *